(12) United States Patent
Frisken

(10) Patent No.: US 11,872,015 B2
(45) Date of Patent: Jan. 16, 2024

(54) APPARATUS AND METHOD FOR CONFOCAL MICROSCOPY USING DISPERSED STRUCTURED ILLUMINATION

(71) Applicant: Cylite Pty Ltd, Notting Hill (AU)

(72) Inventor: Steven James Frisken, Vaucluse (AU)

(73) Assignee: Cylite Pty Ltd, Notting Hill (AU)

( * ) Notice: Subject to any disclaimer, the term of this patent is extended or adjusted under 35 U.S.C. 154(b) by 245 days.

(21) Appl. No.: 17/151,216

(22) Filed: Jan. 18, 2021

(65) Prior Publication Data

US 2021/0137387 A1 May 13, 2021

Related U.S. Application Data

(63) Continuation of application No. 16/313,014, filed as application No. PCT/AU2017/050665 on Jun. 29, 2017, now Pat. No. 10,932,667.

(30) Foreign Application Priority Data

Jul. 1, 2016 (AU) .................................. 2016902602

(51) Int. Cl.
| | |
|---|---|
| G01J 3/447 | (2006.01) |
| A61B 5/00 | (2006.01) |
| A61B 3/10 | (2006.01) |
| G02B 27/00 | (2006.01) |
| A61B 3/00 | (2006.01) |

(Continued)

(52) U.S. Cl.
CPC .............. *A61B 5/0066* (2013.01); *A61B 3/00* (2013.01); *A61B 3/102* (2013.01); *A61B 3/1025* (2013.01); *A61B 3/1225* (2013.01); *A61B 3/18* (2013.01); *A61B 5/0068* (2013.01); *G01J 3/0224* (2013.01); *G01J 3/447* (2013.01); *G01N 21/4795* (2013.01); *G02B 21/0064* (2013.01); *G02B 27/00* (2013.01); *G02B 3/005* (2013.01);

(Continued)

(58) Field of Classification Search
CPC .. A61B 5/0066; A61B 3/102; G01B 9/02091; G01J 3/0224; G01J 3/447; G01J 3/18; G01N 21/4795
See application file for complete search history.

(56) References Cited

U.S. PATENT DOCUMENTS

| | | | |
|---|---|---|---|
| 6,384,916 B1 * | 5/2002 | Furtak ..................... | G01J 3/447 356/369 |
| 7,924,422 B2 * | 4/2011 | Stanke .................. | G01J 3/0297 356/326 |

(Continued)

*Primary Examiner* — Uzma Alam
*Assistant Examiner* — Jonathon Cook
(74) *Attorney, Agent, or Firm* — MATTINGLY & MALUR, PC

(57) ABSTRACT

Methods and apparatus are presented for confocal microscopy using dispersed structured illumination. In certain embodiments the apparatus also comprises an optical coherence tomography (OCT) system, and OCT images acquired from two or more regions of a sample are registered using a corresponding set of two or more larger area images acquired with the confocal microscopy system. In preferred embodiments the apparatus is suitable for analysing the retina of an eye. The confocal microscopy system can be operated in a purely intensity mode or in a coherent mode. In other embodiments a confocal microscopy system using dispersed structured illumination is utilised for surface metrology.

6 Claims, 3 Drawing Sheets

(51) Int. Cl.
 *G02B 21/00* (2006.01)
 *A61B 3/18* (2006.01)
 *G01J 3/02* (2006.01)
 *A61B 3/12* (2006.01)
 *G01N 21/47* (2006.01)
 *G02B 3/00* (2006.01)
 *G02B 27/10* (2006.01)
 *G02B 5/18* (2006.01)

(52) U.S. Cl.
 CPC .. *G02B 27/1086* (2013.01); *G02B 2005/1804* (2013.01)

(56) References Cited

U.S. PATENT DOCUMENTS

| | | | |
|---|---|---|---|
| 9,913,579 B2* | 3/2018 | Frisken | G01B 9/02091 |
| 2005/0174573 A1* | 8/2005 | Harvey | G01J 3/2823 |
| | | | 356/328 |
| 2014/0078298 A1* | 3/2014 | Kudenov | G02B 5/1833 |
| | | | 359/325 |
| 2015/0168210 A1* | 6/2015 | Dorschner | G01J 1/42 |
| | | | 250/225 |
| 2015/0355027 A1* | 12/2015 | Beghuin | G01J 3/2823 |
| | | | 356/453 |
| 2016/0345820 A1* | 12/2016 | Frisken | A61B 3/0025 |
| 2017/0010159 A1* | 1/2017 | Jin | G01J 3/447 |
| 2017/0155873 A1* | 6/2017 | Nguyen | G01J 3/2803 |

\* cited by examiner

APPARATUS AND METHOD FOR CONFOCAL MICROSCOPY USING DISPERSED STRUCTURED ILLUMINATION

CROSS REFERENCE TO RELATED APPLICATIONS

This application is a continuation of U.S. Ser. No. 16/313,014 filed 22 Dec. 2018, which was a 371 of International Application PCT/AU2017/050665 filed on 29 Jun. 2017 which claimed priority to AU 2016902602 filed 1 Jul. 2016, the entire contents of each of which are herein incorporated by reference.

RELATED APPLICATIONS

The present application claims priority from Australian Provisional Patent Application No 2016902602 entitled 'Apparatus and method for confocal microscopy using dispersed structured illumination' filed on 1 Jul. 2016, the contents of which are incorporated herein by reference.

FIELD OF THE INVENTION

The present invention relates to apparatus and methods for confocal microscopy using dispersed structured illumination, in particular for the registration of co-acquired optical coherence tomography (OCT) images. However it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Optical coherence tomography (OCT) is a widely used interferometric technique for studying biological samples including in vivo tissue such as the human eye, with lateral and depth resolution, using information contained within the amplitude and phase of reflected or scattered light. OCT systems generally utilise a Michelson interferometer configuration, with two main approaches being employed: time domain OCT and spectral domain OCT.

In time domain OCT coherence properties of a partially coherent source such as a superluminescent light emitting diode (SLED) with a coherence length of several microns are utilised by interfering light reflected from a sample with a reference beam provided by the same source, but with a time-varying path length. At a specific depth in the sample corresponding to the path length delay in the reference arm, an interference envelope of fringes will be detected in the combined back-reflected signal, allowing the reflection profile in the depth dimension to be reconstructed. Commonly this is done for only a single sample point at a time, and the corresponding scan of depth is known as an 'A-scan'.

Instead of scanning a delay line, spectral domain OCT techniques analyse the reflected light by interfering it with a reference beam, either as a time-varying function of wavelength (swept source OCT) or by dispersing the different wavelengths with a grating or other spectral demultiplexer and detecting them simultaneously along a detector array. The spectral domain information is the Fourier transform of the spatial (depth) reflection profile, so the spatial profile can be recovered by a Fast Fourier Transform (FFT). Generally speaking, spectral domain OCT systems are preferred over time domain OCT systems because they have a ~20 to 30 dB sensitivity advantage.

OCT techniques can be adapted to provide a laterally resolved 'B-scan' by scanning the sample beam relative to the sample in one axis, or a 'C-scan' by scanning in two axes. Faster acquisition is generally desirable irrespective of the type of scan, especially for reducing motion-induced artefacts with in vivo samples, and has been greatly improved over the previous 20 to 25 years by advances in several fields including faster swept source scanning rates and photodetector array readout speeds. However a fundamental limitation with scanning spot schemes, especially for in vivo applications, is presented by laser safety regulations: reducing dwell time to increase scanning speed without being able to increase the applied power will inevitably degrade the signal to noise ratio.

Consequently there has also been research into 'parallelised' OCT systems in which an extended sample area is probed with lateral resolution, or an array of sample spots probed simultaneously. It is relatively straightforward to parallelise time domain OCT, e.g. by utilising a CCD camera and imaging optics as described in U.S. Pat. No. 5,465,147 entitled 'Method and apparatus for acquiring images using a CCD detector array and no transverse scanner'. This provides a two dimensional (2-D) en face image, with depth resolution provided by scanning the reference mirror as usual in time domain OCT.

Swept source spectral domain OCT can be parallelised in similar fashion, as described in Bonin et al 'In vivo Fourier-domain full-field OCT of the human retina with 1.5 million A-lines/s', *Optics Letters* 35(20), 3432-3434 (2010). However because each frame corresponds to a single wavelength, the acquisition time for each A-scan is equal to the frame period times the number of k-points (wavelength samples) acquired. Even for very high speed cameras with frame rates of 100 s of kHz, this can lead to A-scan acquisition times of many ms which can lead to motion artefacts especially with in vivo samples. Published PCT patent application No WO 2016/094940 A1, entitled 'Multichannel optical receivers', discloses an alternative parallelised swept source OCT scheme that enables faster acquisition. In one particular implementation a plurality of spots on a sample are illuminated simultaneously and the reflected or scattered signal light mixed with a reference beam to form a plurality of interferograms with unique carrier frequencies.

Spectrometer-based spectral domain OCT is somewhat more difficult to parallelise because of the necessity to disperse wavelength across many pixels of a 2-D sensor array. In a configuration described in published US patent application No 2014/0028974 A1 entitled line-field holoscopy', cylindrical lenses are used to produce a line illumination on a sample and on a reference mirror. Dispersion of the combined return sample and reference beams along one axis of a 2-D sensor array enables single shot B-scan acquisition. However for full three-dimensional (C-scan) imaging the illuminated line needs to be scanned in the orthogonal direction and the 2-D sensor array read out repeatedly, and it is generally difficult to retain phase coherence between the repeated linear scans.

Single shot C-scan acquisition can be achieved if a 2-D sample area is illuminated and the combined returning sample and reference wavefronts sampled in the two lateral dimensions, e.g. with a 2-D lenslet array, and the resulting sampling points dispersed onto separate sets of pixels of a 2-D sensor array. The effect of this general scheme is to squeeze data from three spatial dimensions, equivalent to two lateral dimensions and one spectral dimension, onto a 2-D sensor array. A mapping of dispersed sampling points onto separate sets of pixels can be ensured by appropriate positioning of the sampling points with respect to the wavelength dispersive element. U.S. Pat. No. 9,243,888 entitled 'Image mapped optical coherence tomography' discloses an alternative approach in which an 'image mapper' having a number of differently angled facets reflects light from different portions of an image onto different areas of a dispersive element and thence onto separate sets of pixels of a 2-D sensor array.

Configurations for applying a lenslet-based sampling technique to single shot acquisition of images from small volumes of order 100 µm×100 µm×1000 µm from retinal and other samples are disclosed in published US patent application No 2016/0345820 A1 entitled 'High resolution 3-D spectral domain optical imaging apparatus and method' and Anderson et al '3D-spectral domain computational imaging', Proc SPIE 9697 (8 Mar. 2016) http://dx.doi.org/10.1117/12.2214801. The combined returning wavefronts are sampled with a rectilinear lenslet array angled with respect to the dispersive axis of a dispersive element, with the sampling being in either the Fourier plane, i.e. the far field, providing a form of 'holoscopy', i.e. holographic OCT, or the image plane, i.e. the near field. In either case the spatial resolution depends largely on the NA of the objective lens, and may for example be around 3 µm. Illuminated areas on the sample are preferably kept relatively small, of order 100 µm×100 µm, to reduce the impact of multiple scattering and also because of the limited number of sampling points offered by commercially available lenslet arrays. Images of multiple adjacent or overlapping volumes can in principle be acquired and stitched together to image larger sample volumes, but the total acquisition speed is limited by the frame rate of the 2-D sensor array. Although acquisition of individual volumes can be fast, of order 0.1 ms, for reasonably cost effective electronics the frame rate currently limits the acquisition rate to a few 100 Hz. Since eye motion can be significant on the ms time scale, improved registration techniques are required to allow a larger area of a retina to be acquired by stitching together frames without loss of registration. Improved registration techniques would also be advantageous to provide a clinical user with a broader view of a retina during setup, while identifying areas of interest. While a separate optical image of the retina could be obtained and multiplexed into an OCT image, this would provide inferior resolution detail and the separate imaging systems are not tightly integrated.

Unless the context clearly requires otherwise, throughout the description and the claims the words 'comprising', 'comprises' and the like are to be construed in an inclusive sense as opposed to an exclusive or exhaustive sense. That is, they are to be construed in the sense of 'including, but not limited to'.

OBJECT OF THE INVENTION

It is an object of the present invention to overcome or ameliorate at least one of the limitations of the prior art, or to provide a useful alternative. It is an object of the present invention in a preferred form to provide apparatus and methods for acquiring optical coherence tomography images of extended sample volumes by stitching together two or more images without loss of registration. It is another object of the present invention in a preferred form to provide apparatus and methods for analysing a sample using a dispersed structured illumination field.

SUMMARY OF THE INVENTION

According to a first aspect of the present invention there is provided an apparatus for analysing a sample, said apparatus comprising a confocal microscopy system comprising:
   a first optical system comprising one or more optical sources for emitting light in a first wavelength band and a wavelength dispersive element for generating, at a first region of a sample, a dispersed structured illumination field in the form of a grid of beamlets for each wavelength within said first wavelength band;
   a second optical system for collecting light from said dispersed structured illumination field reflected or scattered from said first region of said sample, compensating for the spectral dispersion imposed by said wavelength dispersive element and passing the dispersion compensated collected light through at least one aperture; and
   a spectrometer comprising a two-dimensional sensor array for spectrally analysing the collected light reflected or scattered from said first region of said sample.

In certain embodiments the confocal microscopy system is configured to analyse a structure in the posterior segment of an eye such that, in use, the optical power elements of the eye cooperate with the first optical system to generate the dispersed structured illumination field at the structure. In a preferred embodiment the confocal microscopy system is configured to analyse the retina of an eye.

In certain embodiments the first optical system is configured to disperse the light in the first wavelength band along a direction at an angle to an axis of a grid of beamlets, for generating a dispersed structured illumination field that is substantially contiguous over the first region.

In certain embodiments the apparatus comprises an optical coherence tomography (OCT) system for performing an OCT analysis of the sample at a second region that is at least partially overlapping with the first region. In preferred embodiments the OCT system utilises light in a second wavelength band, different from the first wavelength band, for dispersion onto different portions of the two-dimensional sensor array. Preferably, the OCT system comprises a light source for emitting light in the second wavelength band. In alternative embodiments the confocal microscopy system and the OCT system are configured to analyse the sample utilising light in different polarisation states.

The spectrometer is preferably common to the OCT system and the confocal microscopy system. Preferably, the OCT system is configured to sample in the Fourier field light reflected or scattered from the second region of the sample. Preferably, the OCT system comprises an aperture for filtering out light that is outside the spatial Nyquist limit of an analysis system of the OCT system.

In preferred embodiments the apparatus is configured to move the dispersed structured illumination field and a sample beam of the OCT system relative to the sample, for acquiring a plurality of confocal microscopy and OCT images of successive first and second regions of the sample. The apparatus is preferably configured to acquire, for each position of the dispersed structured illumination field and the sample beam on the sample, a confocal microscopy image and an OCT image in a single frame of the two-dimensional sensor array. Preferably, the apparatus comprises a processor adapted to register the plurality of OCT images using information obtained from the plurality of confocal microscopy images. In preferred embodiments each of the second regions is wholly within a respective first region.

Preferably, the apparatus comprises an optical splitter for splitting off a portion of light from the one or more optical sources to form a reference beam for interfering with light in the first wavelength band reflected or scattered from the sample.

In certain embodiments the first optical system is configured to disperse the light in the first wavelength band along a direction substantially parallel to an axis of a grid of beamlets, for generating a dispersed structured illumination field comprising one or more overlapping sequences of dispersed wavelengths spaced apart on the sample.

In certain embodiments the wavelength dispersive element has optical power for enabling wavelength-dependent focusing of the dispersed structured illumination field. Preferably, the apparatus comprises a processor adapted to use the overlapping of the sequences of dispersed wavelengths at one or more points on the sample to provide a subsampled optical spectrum for interferometric detellnination of an axial position at the one or more points. The apparatus is preferably configured to move the dispersed structured illumination field relative to the sample, for analysing additional regions of the sample.

In certain embodiments the first optical system comprises an optical source and a lenslet array for producing a grid of beamlets containing light in the first wavelength band. In other embodiments the first optical system comprises a plurality of optical sources for producing a grid of beamlets containing light in the first wavelength band.

According to a second aspect of the present invention there is provided a method for analysing a sample, said method comprising the steps of:
generating at a first region of said sample, using one or more optical sources emitting light in a first wavelength band and a wavelength dispersive element, a dispersed structured illumination field in the form of a grid of beamlets for each wavelength within said first wavelength band;
collecting light from said dispersed structured illumination field reflected or scattered from said first region of said sample;
compensating for the spectral dispersion imposed by said wavelength dispersive element;
passing the dispersion compensated collected light through at least one aperture; and
spectrally analysing the collected light reflected or scattered from said first region of said sample using a spectrometer comprising a two-dimensional sensor array.

In certain embodiments the sample comprises a structure in the posterior segment of an eye. Preferably, the sample comprises the retina of an eye.

In preferred embodiments the method further comprises the step of performing an OCT analysis of the sample at a second region that is at least partially overlapping with the first region. Preferably, the method further comprises the steps of moving the dispersed structured illumination field and a sample beam used for the OCT analysis relative to the sample and acquiring a plurality of confocal microscopy and OCT images of successive first and second regions of the sample. Preferably, for each position of the dispersed structured illumination field and the sample beam on the sample, a confocal microscopy image and an OCT image are acquired in a single frame of the two-dimensional sensor array. In preferred embodiments the method further comprises the step of registering the plurality of OCT images using information obtained from the plurality of confocal microscopy images.

According to a third aspect of the present invention there is provided an apparatus for performing optical coherence tomography (OCT) imaging across an extended region of a sample, said apparatus comprising:
  a first optical system comprising one or more optical sources for emitting light in a first wavelength band and a wavelength dispersive element for generating, at a first region of a sample, a dispersed structured illumination field in the form of a grid of beamlets for each wavelength within said first wavelength band;
  a second optical system for collecting light from said dispersed structured illumination field reflected or scattered from said first region of said sample and compensating for the spectral dispersion imposed by said wavelength dispersive element;
  a spectrometer comprising a two-dimensional sensor array for spectrally analysing the collected light reflected or scattered from said first region of said sample;
  an OCT system for acquiring an OCT image of said sample at a second region that is at least partially overlapping with said first region;
  a mechanism for moving said dispersed structured illumination field and a sample beam of said OCT system across said sample so as to collect light reflected or scattered from at least one additional first region and to acquire an OCT image from at least one additional second region; and
  a processor adapted to use information obtained from the spectral analysis of the collected light from two or more first regions to register OCT images acquired from two or more second regions.

According to a fourth aspect of the present invention there is provided a method for performing optical coherence tomography (OCT) imaging across an extended area of a sample, said method comprising the steps of:
  (i) generating at a first region of said sample, using one or more optical sources emitting light in a first wavelength band and a wavelength dispersive element, a dispersed structured illumination field in the form of a grid of beamlets for each wavelength within said first wavelength band;
  (ii) collecting light from said dispersed structured illumination field reflected or scattered from said first region;
  (iii) compensating for the spectral dispersion imposed by said wavelength dispersive element;
  (iv) spectrally analysing the collected light reflected or scattered from said first region;
  (v) obtaining, with an OCT system having a sample beam that illuminates said sample, an OCT image of a second region of said sample, wherein said second region is at least partially overlapping with said first region;
  (vi) moving said dispersed structured illumination field and said sample beam relative to said sample and repeating steps (i) to (v) for at least one additional first region and at least one additional second region; and
  (vii) using information obtained from the spectral analysis of the collected light from two or more first regions to register the OCT images acquired from two or more second regions.

According to a fifth aspect of the present invention there is provided a spectrometer for analysing the spectra of a plurality of polarised light beams, said spectrometer comprising:

a polarisation beam splitter for directing optical power according to polarisation state;

a wavelength dispersive element for dispersing a plurality of polarised light beams;

a polarisation transformation system for transforming the polarisation of said plurality of polarised light beams; and a two-dimensional sensor array for recording the spectra of said plurality of polarised light beams, wherein said spectrometer is configured such that, in use, said polarisation beam splitter directs incoming polarised light beams to said wavelength dispersive element and directs the dispersed polarised light beams to said two-dimensional sensor array.

Preferably, the wavelength dispersive element comprises a grating. In preferred embodiments the polarisation transformation system comprises a mirror and a quarter wave plate configured such that, in use, the plurality of polarised light beams traverse the quarter wave plate before and after being reflected from the mirror. The spectrometer preferably comprises a focusing element for imaging the spectral components of the dispersed polarised light beams onto the two-dimensional sensor array. In certain embodiments the spectrometer comprises a polariser for analysing the polarisation of the plurality of polarised light beams before the polarised light beams traverse the polarisation beam splitter. Preferably, the wavelength dispersive element is oriented such that each light beam in the plurality of polarised light beams is dispersed onto a separate set of pixels of the two-dimensional sensor array.

According to a sixth aspect of the present invention there is provided an article of manufacture comprising a computer usable medium having a computer readable program code configured to operate the apparatus according to the first or third aspect, or to implement the method according to the second or fourth aspect.

BRIEF DESCRIPTION OF THE DRAWINGS

Preferred embodiments of the invention will now be described, by way of example only, with reference to the accompanying drawings in which.

DETAILED DESCRIPTION OF THE INVENTION

As mentioned in the Background section, OCT-based techniques for acquiring single snapshot 3-D images of relatively small volumes of a sample such as a retina, typically with illuminated areas of order 100 µm×100 µm, have been disclosed in Anderson et al Proc SPIE 9697 (8 Mar. 2016) http://dx.doi.org/10.1117/12.2214801 and published US patent application No 2016/0345820 A1. Larger volumes can in principle be imaged by stitching together images of adjacent or slightly overlapping volumes, but this can be adversely affected by sample movement especially for in vivo samples such as the human eye. To overcome this limitation we present a registration and viewing technique that provides snapshot measurements with spatial resolution comparable to that offered by confocal microscopy systems such as scanning laser ophthalmoscopes (SLOs), but without requiring high speed laser sampling which can have its own motion artefacts.

Figure 1:
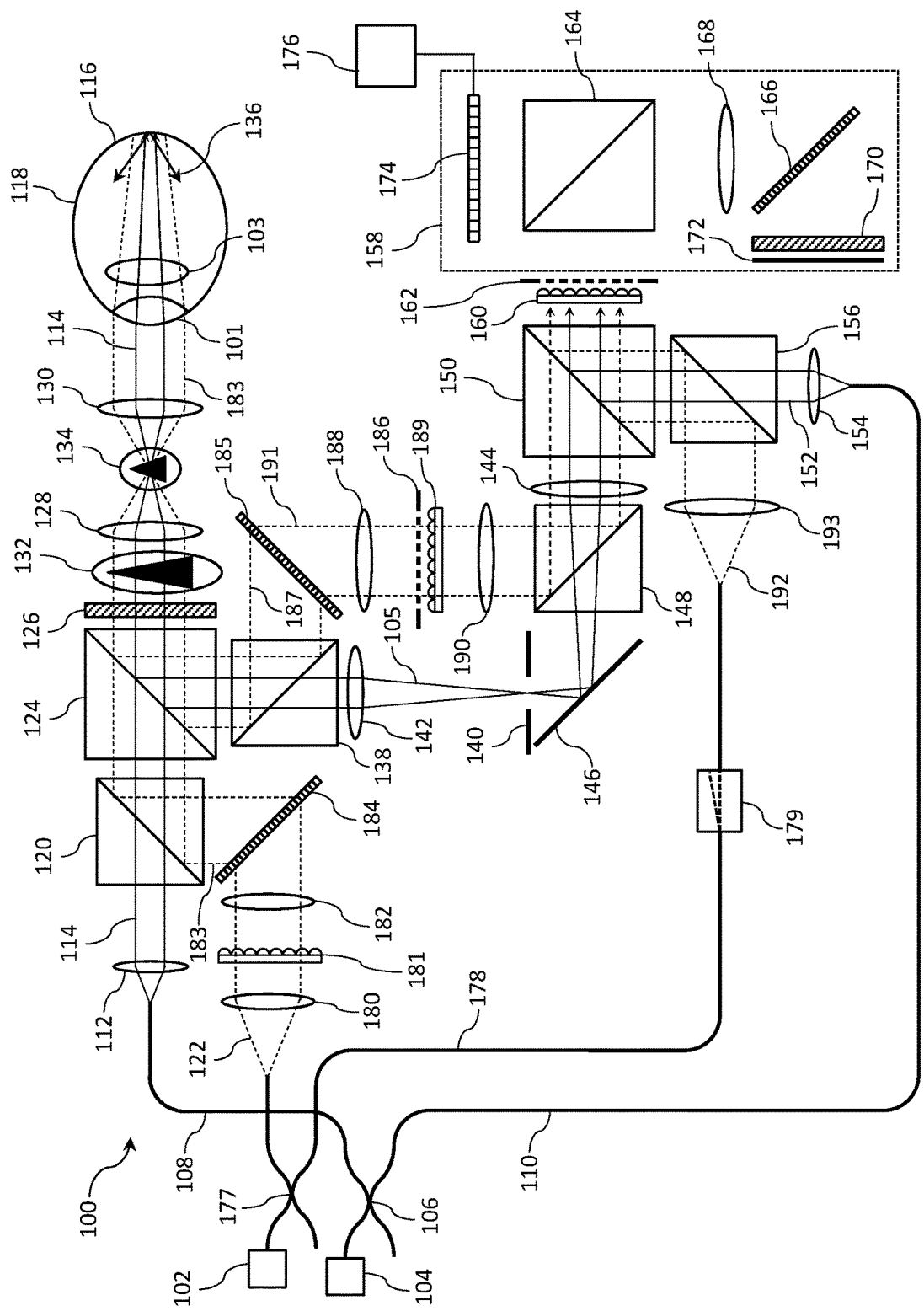
FIG. 1 illustrates in schematic form an apparatus comprising integrated confocal microscopy and spectral domain OCT systems for examining the retina of an eye.

FIG. 1 shows in schematic form an apparatus 100 comprising integrated confocal microscopy and spectral domain OCT systems for examining one or more structures in the posterior segment of an eye 118. The apparatus is particularly suitable for examining the retina 116 and will be described with reference to this application, but it is also suitable for examining other posterior segment structures such as the choroid. In this example embodiment we employ wavelength multiplexing for the two systems, with first and second optical sources 102, 104 emitting light in first and second wavelength bands that are different from each other for dispersion onto different portions of a 2-D sensor array 174. In an alternative embodiment different wavelength bands are obtained from a single optical source using wavelength-selective optics such as an optical fibre or bulk optics dichroic splitter. Wavelength multiplexing enables confocal microscopy and OCT data to be acquired simultaneously, which is preferred for reliable compensation of ocular motion as described below. In preferred embodiments each of the first and second wavelength bands comprises a single range of wavelengths, while in other embodiments they are interleaved. In other embodiments not described in detail herein, orthogonal polarisation states or fast time multiplexing could be used instead of wavelength multiplexing for the confocal microscopy and OCT systems. For example polarisation demultiplexing could be used to separate an illumination beam into two polarisation states and encode the angularly dispersed confocal microscopy portion of the light into one polarisation state before a polarisation recombining element recombines the light which is subsequently directed to the sample. In this embodiment, not further described herein, the detection system resolves both polarisation states in the reflected light to enable an integrated confocal microscopy and OCT system.

In preferred embodiments the optical sources emit light in the near IR spectral region, however in general light in the IR, visible or UV spectral regions could be used depending on the application.

We first describe the operation of a high-resolution spectral domain OCT imaging system operating with light of wavelength around 870 nm. In the system as described, an OCT image of a retina 116 is obtained using a 'holoscopic' technique in which the Fourier plane of the image is captured and a fast Fourier transform (FFT) employed to simulate mathematically the role of a physical lens to construct a high-resolution image of the retina. Near field techniques can alternatively be used. Light from a second optical source 104 in the form of an optical fibre coupled superluminescent diode (SLD) with centre wavelength 870 nm and bandwidth of approximately 40 nm is split by a 90/10 ratio 2×2 coupler 106 into a sample path 108 (90%) and a reference path 110 (10%). Path length matching conditions will generally be required for the interference portion of the OCT system, and can be achieved by adjusting the lengths of the respective optical fibre paths during manufacture or by providing length adjusting means such as switchable delay lines for example. Light from the sample path fibre 108 is collimated by a lens 112 to form a relatively small diameter sample beam 114 of, say, several 100 μm FWHM, corresponding inversely proportionally to the desired illumination spot size on the retina 116 of a sample eye 118. That is, a smaller diameter sample beam will produce a larger illumination spot size on the retina. A dichroic optic in the form of a dichroic beam splitter 120 designed to pass light of 870±18 nm and reflect light of 840±8 nm allows the sample beam 114 to be combined with light 122 from a first optical source 102 to be described later. Other dichroic beam splitters 138, 148 and 156 in the apparatus are of similar design to the dichroic beam splitter 120.

The sample beam 114 passes through a polarisation beam splitter (PBS) 124 and a quarter wave plate 126 before being relayed to the sample eye 118 via a 4F lens system comprising lenses 128 and 130. In certain embodiments the polarisation of light from the second optical source 104 is controlled, e.g. with a fibre optic polarisation controller or a linear polariser (not shown), to maximise its transmission through the PBS 124 towards the sample eye 118. Adjustment of the position and angle of light incident on the retina 116 can be achieved via beam steering optics such as angular deflection devices 132 and 134, which for convenience are depicted here as transmissive devices such as prisms although non-dispersive reflective devices such as angularly adjustable mirrors are generally to be preferred. The first deflection device 132 allows the sample beam 114, and the corresponding reflected beam that returns along the same path, to be moved to different positions on the retina 116. The second deflection device 134 allows the angle of illumination on the retina to be adjusted, which can be important in achieving improved image quality through reduction of speckle and enhancement of resolving power. Additional power elements may be inserted into the relay to accommodate for variations of the eye under test as would be well understood in the art.

A portion of the light 136 from the sample beam 114 reflected or scattered from the retina 116 is collected and passes back through the relay. The returning light then traverses the quarter wave plate 126 a second time so that a significant fraction of it is polarised orthogonally to the incoming sample beam 114, for direction by the PBS 124 through a dichroic beam splitter 138 towards an optional holoscopy aperture 140 located at a position that, in use, corresponds to the 8F retinal plane as defined by the combination of lenses 142, 128, 130 and the optical power elements of the eye 118, i.e. its lens 103 and cornea 101. Although optional, this aperture 140 advantageously serves to filter out light that is outside the spatial Nyquist limit of the subsequent analysis system and might otherwise contribute to phantom signals or noise. Although the holoscopy aperture 140 is shown as being located at the 8F retinal plane, it could alternatively be positioned elsewhere, for example at the 12F retinal plane.

The relayed retinal image is then collimated by a lens 144 after being reflected by a mirror 146 and transmitted through a dichroic beam splitter 148. A beam splitter 150, preferably but not necessarily a polarisation beam splitter (PBS), allows the far field of the retinal image to be combined with a suitably path length adjusted reference beam 152 that is collimated by a lens 154 and passes through a dichroic beam splitter 156. The far field of the retinal image is then compared to the reference beam 152 using a spectrometer 158 capable of analysing the polarisation state of the combined beams at a grid of spatial positions determined by a spatial sampling element such as a two-dimensional (2-D) lenslet array 160, preferably in combination with a corresponding 2-D aperture array 162 for reducing stray light. The polarisation state of the combined beams is analysed by a PBS 164 which is adjusted to be at an angle to both polarisation states, thereby creating an interference between the reference and signal paths which can provide information on the relative phase across the far field of the retinal image. The spectrometer 158 used here is a compact reflective spectrometer able to analyse a plurality of grid points, beams or beamlets simultaneously as they are dispersed at an angle to the grid by an appropriately oriented wavelength dispersive element in the form of a transmissive grating 166. A focusing element such as a lens 168 or an off-axis parabolic mirror collimates the grid of points for dispersion by the grating 166, followed by double passage through a quarter wave plate 170 via reflection from a mirror 172 to rotate the polarisation state by 90 degrees. In combination the quarter wave plate 170 and the mirror 172 form a polarisation transformation system, which in this particular example effects a polarisation transformation comprising a 90 degree rotation. The dispersed spectral components of the reflected light are imaged by the lens 168 onto a 2-D sensor array 174 such as a CMOS camera after passing through the PBS 164. The interferogram detected by the 2-D sensor array is read out in a single frame for subsequent analysis by a processor 176 equipped with suitable machine-readable program code. The processor may for example apply well-known Fourier transform techniques to obtain a depth-resolved image, i.e. a three-dimensional (3-D) image of a volume corresponding to the area of the retina 116 illuminated by the sample beam 114. In preferred embodiments the grating 166 is oriented with respect to the grid of spatial positions determined by the 2-D lenslet array 160 and the corresponding 2-D aperture array 162 such that each of the combined beams entering the spectrometer 158 is dispersed onto a separate set of pixels of the two-dimensional sensor array 174.

In broad terms the spectrometer 158 is configured for dispersion and polarisation transformation of light at a grid of sampling points, where the dispersion allows analysis of different wavelengths and the polarisation transformation enables redirection of optical power at a polarisation beam splitter. Advantageously, it provides a low-loss and compact realisation of a grid-sampling spectrometer where the polarisation beam splitter can provide the additional function of the interference analyser.

We now describe the operation of a confocal microscopy system using dispersed structured illumination, and its integration with the above-described holoscopic spectral domain OCT imaging system. In the particular embodiment described with reference to FIG. 1 the confocal microscopy system utilises light 122 from a first optical source 102 in the form of an optical fibre coupled SLD with centre wavelength 840 nm and bandwidth of approximately 16 nm. Optionally, a portion e.g. 10% of the light from this source is split off with a 2×2 coupler 177 into a reference path 178 if interferometric measurement is desired, e.g. for higher sensitivity or to obtain relative phase measurements for example for angiographic phase contrast measurements. This optional reference path 178 may also include an optical switch 179 to block the reference beam for non-interferometric measurements, as well as path length adjustment means such as switchable delay lines for interferometric measurements.

Figure 2A:
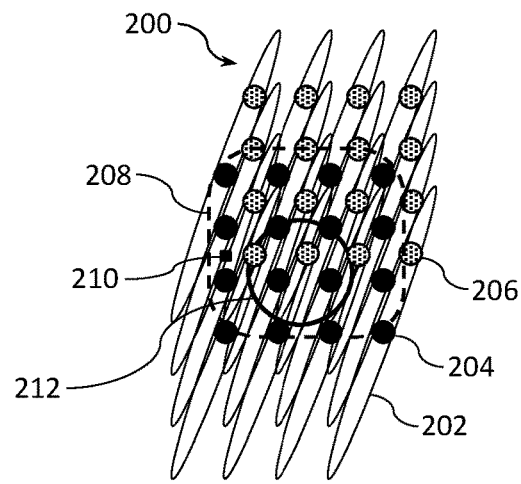
FIG. 2A shows in schematic form a preferred illumination pattern on a sample retina formed by light from the integrated confocal microscopy and spectral domain OCT systems shown in FIG. 1.

Light 122 from the first source 102 is collimated by a lens 180 into a relatively large beam, e.g. several mm in diameter and preferably larger in diameter than the OCT sample beam 114, then launched into a spatial sampling element such as a 2-D lenslet array 181 and Fourier transformed by a subsequent lens 182. The Fourier transformed sample beamlets are dispersed by a wavelength dispersive element in the form of a transmissive grating 184 and coupled into the same train as the holoscopic OCT system by the dichroic beam splitter 120. Importantly, the lenslet array 181 and the grating 184 are preferably angled with respect to each other so that, as described below, the grid of dispersed sample beamlets 183 will provide a dispersed structured illumination field that covers an extended and preferably substantially contiguous region when reimaged onto the retina 116 of the sample eye 118. The grid of wavelength-dispersed Fourier transformed sample beamlets, represented schematically by the envelope 183, is relayed to the eye 118, analogously to the OCT sample beam 114, by the optical relay system comprising lenses 128, 130 and deflectors 132, 134. The optical power elements of the eye then act on the dispersed sample beamlets to generate at the retina 116, as shown in FIG. 2A, a dispersed structured illumination field 200 in the form of a grid of beamlets for each wavelength within the first wavelength band, i.e. within the wavelength band emitted by the first source 102. Representative grids of beamlets for two particular wavelengths within the dispersion envelope 202 of the first wavelength band are indicated by the arrays of points 204 and 206. When the lenslet array 181 and the grating 184 are suitably angled with respect to each other as noted above, the dispersed structured illumination field 200 can be made substantially contiguous over a first region 208 on the retina. That is, within this first region there are few or no parts of the retina not illuminated by the dispersed structured illumination field. Each combination of grid point plus wavelength defines a specific location 210 on the retina, with some redundancy since the dispersion envelopes 202 are partially overlapping at least within a portion of the first region 208. The sample beam 114 of the OCT imaging system illuminates a second region 212 of the retina that is at least partially overlapping with the first region 208. Preferably the second region 212 is wholly within a larger first region 208 as shown, so that every point on the retina illuminated by the OCT beam 114 is also illuminated by the dispersed structured illumination field 200 of the confocal microscopy system. In certain embodiments the first region 208 may be ten to several hundred times larger than the cumulative area of the second region 212. The second region may be contiguous as shown, or a grid of sampling points (A-scans), generated for example by a lenslet array or other spatial sampling element in the OCT optics train (not shown in FIG. 1), each of a given area, providing a cumulative area. Returning to FIG. 1, in certain embodiments some optical power can be provided by appropriate design of the grating 184, e.g. a degree of chirp, which would allow the redundant wavelengths to be imaged at different depths to give greater tolerance to variations in the ocular power of the eye 118 being analysed.

When the apparatus 100 is being used to analyse the retina 116 an eye 118 as shown in FIG. 1, the optical power elements of the eye, i.e. the cornea 101 and the lens 103, cooperate with the lenslet array 181, the Fourier transforming lens 182, the grating 184 and other optical components in the train to generate the dispersed structured illumination field at the retina 116. For analysing a non-ocular sample the apparatus 100 may include an additional focusing element in lieu of the optical power elements of the eye. Similarly, for analysing a structure in the anterior segment of an eye, such as the sclera, the anterior or posterior corneal surface or the anterior or posterior lens surface, the apparatus 100 may include an additional focusing element in lieu of some or all of the optical power elements of the eye as appropriate. These additional focusing elements would also serve to focus the OCT sample beam 114 onto the sample.

As opposed to the 3-D holoscopic measurement provided by the OCT imaging system, the dispersed structured illumination field 200 as shown in FIG. 2A enables a confocal measurement at each illuminated point 210 on the retina 116. However to obtain the confocal measurement we need to create a pinhole or aperture array that can act on all wavelengths simultaneously. This is provided by a second optical system comprising a dispersive element in the form of a transmissive grating 185 for unwinding the dispersion imposed by the grating 184, and an aperture array 186 that is preferably tightly correlated with the sampling grid that was created by the lenslet array 181. More broadly, the aperture array 186 needs to have at least one aperture correlated tightly with at least part of the sampling grid generated by the lenslet array 181. The dispersion compensation from the grating 185 occurs after the confocal beamlets 187 collected from the retina 116 have been separated from the returning holoscopic OCT beam 105 by the dichroic beam splitter 138. The lens 188 used to focus the confocal beamlets 187 onto the aperture array 186 may require active focal length adjustment in production to ensure registration at the aperture array 186 over the whole wavelength range and grid points. The second grating 185 also needs to be designed to reverse any optical power that may have been designed into the first grating 184. An optional lenslet array 189 can be used to optimise the projection of the aperture array 186 through the lenslet array 160 and onto the subsequent aperture array 162 with low coupling loss, although adjustments of the lenses 190 and 144 may prove adequate in practice with reasonable efficiency. The grid of dispersion compensated beamlets 191 is recombined with the returning OCT beam 105 in the dichroic beam splitter 148, for analysis by the spectrometer 158. This spectrometer is capable of analysing the grid of confocal microscopy points and the lenslet array 160-sampled returning OCT beam 105 over a range of 830 to 890 nm through design of the dispersive element 166 and the focusing lens 168. It will be appreciated that because the confocal microscopy and OCT systems use light in different wavelength bands, the grid of confocal microscopy points and the sampled returning OCT beam will be projected onto different portions of the 2-D sensor array 174, enabling acquisition of both confocal microscopy and OCT data within a single frame of the 2-D sensor array.

Figure 2B:
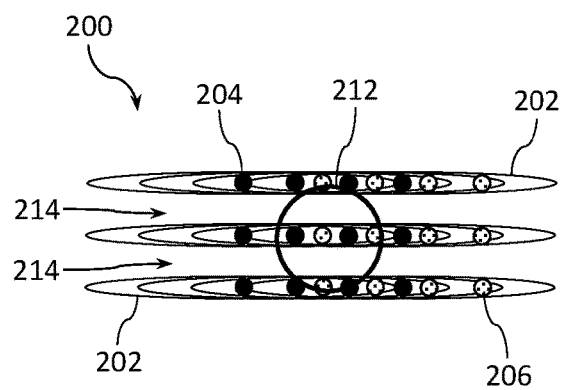
FIG. 2B shows in schematic form another illumination pattern formed by light from the integrated confocal microscopy and spectral domain OCT systems shown in FIG. 1.

As mentioned above and with reference to FIG. 2A, adjustment of the angular deflection device 132 enables the region 212 illuminated by the OCT sample beam 114 to be moved to different positions on the retina 116, enabling examination of larger areas. Since the OCT and confocal microscopy systems are integrated, this adjustment also moves the region 208 illuminated by the dispersed structured illumination field 200 of the confocal microscopy system. Importantly, because the region 212 is at least partially overlapping with, and preferably wholly within a larger region 208, the confocal microscopy system can be utilised to ensure accurate registration of successive volumes illuminated by the OCT sample beam 114. For example the processor 176 may use autocorrelation techniques to determine displacement vectors based on the overlapping images of the larger region 208. If eye movement, say, causes an error in the positioning of the OCT sample beam 114 on the retina, this error can be detected and corrected by matching the larger area retinal images acquired by the confocal microscopy system. It is for the purpose of ensuring accurate registration of successive OCT volumes that the dispersed structured illumination field 200 is preferably angled with respect to the beamlet grids 204, 206 as described above with reference to FIG. 2A. If the dispersion axis of the grating 184 were parallel to an axis of the lenslet array 181 the dispersed structured illumination field 200 at the retina may appear as shown in FIG. 2B. It will be appreciated that in this situation there are gaps 214 in the dispersed structured illumination field 200 where significant portions of a region 212 illuminated by the OCT sample beam would have no overlap with the dispersion envelopes 202.

Within each frame of the 2-D sensor array 174 the actual illumination time can be quite brief, of the order of 100 μs, to reduce any fringe fading due to motion artefacts. For maximum accuracy of registration, a grid of confocal microscopy points and a lenslet-sampled OCT beam are preferably acquired substantially simultaneously e.g. with respective OCT and confocal microscopy images acquired in a single frame of the 2-D sensor array 174. It is also possible for confocal microscopy and OCT images to be acquired in successive frames, e.g. by shuttering of the different wavelength bands obtained from a single broadband source or by pulsing of separate optical sources, although the time between frames should be short so that ocular motion can be reliably compensated. The ability to choose independently the timing of the illumination for the confocal microscopy and OCT systems can be beneficial. In one example, pulsing the confocal microscopy system source 102 at the end of a frame provides the ability to adjust the exact registration of the next frame of the holoscopic OCT measurement through a fine adjustment of the deflection device 132 from the position anticipated based on the shift of the confocal microscopy measurement. The ability to measure and correlate across a large field of the retina 116 allows us to ensure that there are no gaps or stitching errors between separate volumes induced by eye motion. Furthermore we can accurately return to any retinal areas if required for reacquisition. Because the region 208 illuminated by the confocal microscopy system is usually considerably larger than the region 212 illuminated by the OCT system, points on the retina will often appear in several confocal images, possibly hundreds of images.

Advantageously, these multiple exposures enable a highly averaged image to be generated by having measured each point multiple times with different illumination wavelengths, increasing the quality of the image and reducing any speckle artefacts.

The confocal microscopy system can be operated in either a purely intensity mode, i.e. without employing the reference arm 178, as would be the case for a conventional SLO or scanning confocal microscope, or in a coherent mode where the grid of beamlets 191 reflected from the retina 116 is interfered with a reference beam 192 collimated by a lens 193. Noting that a coherent signal can be more easily interpreted if its intensity is known, acquisition in both modes in sequential frames is possible via operation of the optical switch 179. In many cases the purely intensity mode will be preferred, since the interference in the coherent mode can be an unnecessary complication for the registration process. Alternatively it is possible to acquire a phase-resolved interference spectrum to interpret or determine the relative phase and amplitude of the confocal microscopy signal.

It will be appreciated that several elements in the apparatus of FIG. 1 may need to be operated in coordinated fashion, including for example the optical sources 102 and 104, the angular deflection devices 132 and 134, the optical switch 179 and the 2-D sensor array 174. This overall level of control may for example be provided by equipping the processor 176 with suitable machine-readable program code.

In preferred embodiments the spectrometer 158 is common to the integrated OCT and confocal microscopy systems as shown in FIG. 1, to increase integration of the componentry and ensure enhanced registration of the OCT images. However it would be advantageous in some circumstances to have two independent spectrometers, e.g. to enable individual optimisation of each spectrometer.

We note that, for the purposes of registration of successive volumes illuminated by the OCT system, it is not essential for the integrated microscopy system to be confocal. That is, the aperture array 186 and the lenslet array 189 could be omitted from the apparatus 100 to yield an OCT imaging system integrated with a non-confocal microscopy system. However a confocal microscopy system is preferred because of the improved noise rejection and the improved accuracy of registration in the presence of axial displacements.

It will be appreciated that the confocal microscopy and OCT systems of the apparatus 100 can be operated in isolation. For example the confocal microscopy system alone may be used to analyse one or more regions of the retina 116 or other structure in the posterior segment of an eye 118.

Figure 3:
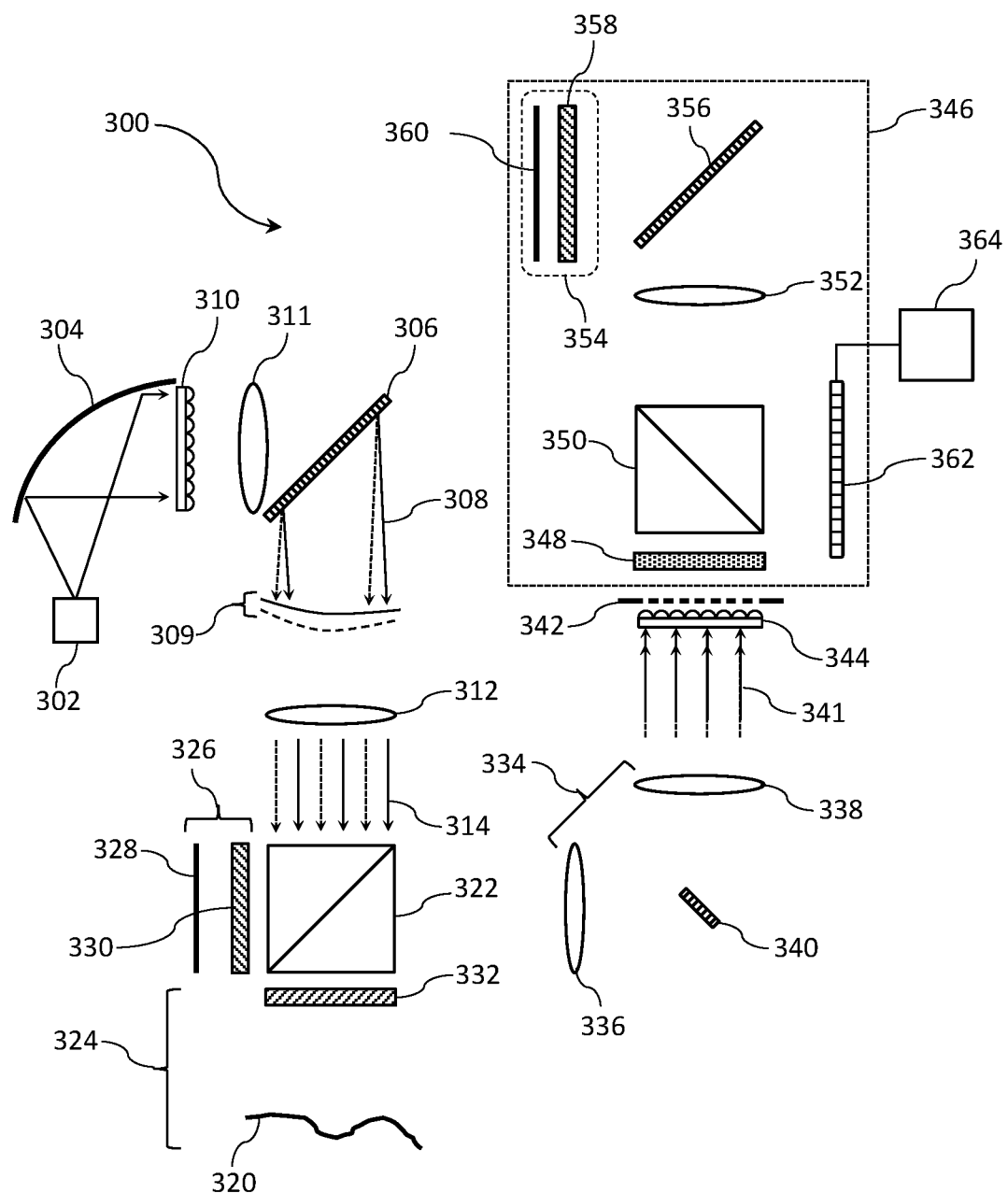
FIG. 3 shows in schematic form a surface metrology apparatus.

The ability to generate a dispersed structured illumination field in the form of a grid of beamlets for each wavelength within a wavelength band, used for registration of repeated snapshot 3-D OCT images as described above, can also be used for metrology applications. FIG. 3 shows in schematic form an apparatus 300 for surface metrology of an object 320. Light from an optical source 302 in the form of a polarised superluminescent light emitting diode (SLED) with centre wavelength 840 nm and a bandwidth of approximately 20 nm is collimated by an off-axis parabolic mirror 304 then passed through a spatial sampling element such as a 2-D lenslet array 310 or an array of diffractive optical elements (DOEs) to produce a grid of sample beamlets. The sample beamlets are relayed through a system of lenses 311 and 312 which can be magnifying or reducing, depending on the application, through choice of focal length. A wavelength dispersive element in the form of a transmissive grating 306 having, say, 1500 lines/mm, is provided within the lens relay. The optical source 302, lenslet array 310, grating 306 and lenses 311, 312 in combination form an optical system that generates a dispersed structured illumination field 314 in the form of a grid of beamlets for each wavelength within the emission band of the source. That is, each wavelength component of the source 302 will have a corresponding grid which is offset in the dispersive axis of the grating 306. In an alternative embodiment a grid of sample beamlets for generating the dispersed structured illumination field is provided by a plurality of optical sources such as an array of LEDs. The dispersed structured illumination field 314 proceeds to the sample 320 via a beam splitter, preferably but not necessarily a polarisation beam splitter (PBS) 322, that splits it into a sample arm 324 and a reference arm 326, and the reflections from the sample 320 and the reference arm mirror 328 are recombined by the PBS 322 after rotation of their respective polarisations by the quarter wave plates 330 and 332.

In certain embodiments the transmissive grating 306 is designed to provide optical power in one or two axes through curvature of the lines or a chirped line spacing, or both, as is known in the art. In this case the optical power of the grating is a function of wavelength, so that any subsequent focusing of the light will have an effective wavelength-dependent focal plane as represented by the curved wavefronts 309. This feature is particularly advantageous for an industrial metrology system where samples may have large surface fluctuations, as it permits high transverse resolution over an extended depth of focus by using the chromatic focusing in combination with the phase information of the light at multiple wavelengths, which can be accessed through an interferometric OCT measurement described below.

In the metrology apparatus 300 the grating 306 and lenslet array 310 are preferably oriented with respect to each other such that the dispersive axis of the grating is aligned with an axis of the lenslet array. This is in contrast to the previously described confocal microscopy/OCT apparatus 100 shown in FIG. 1, where the dispersive axis of the grating 184 is preferably at an angle to an axis of the lenslet array 181. As depicted schematically in FIG. 4, dispersion along an axis of the lenslet array results in a dispersed structured illumination field 400 having overlapping sequences of dispersed wavelengths 402 spaced apart on a series of projection lines 404, for interaction with a sample. Similar to the situations shown in FIGS. 2A and 2B, the arrays of points 406 and 408 represent grids of beamlets for two particular wavelengths within the dispersion envelope 410 of the wavelength band emitted by the source 302.

The combined reflected reference and sample light fields are transformed through a dispersive optical relay 334 comprising relay lenses 336 and 338 and a numerical aperture limiting grating 340 designed to compensate the spectral dispersion and any chromatic focusing imposed by the grating 306. This enables all wavelengths in the grid of dispersion compensated beamlets 341 to be simultaneously apertured by an aperture grid 342 designed to correspond to the illuminating grid produced by the lenslet array 310. The size of the apertures in the aperture grid 342 and the size of the dispersive relay aperture defined by the grating 340 are chosen to optimise collection of light from a sufficient depth of field at the sample 320 and reduce crosstalk from multiply-scattered light. Generally, smaller apertures provide enhanced depth of field and reduced lateral resolution, along with lower signal levels. In one particular example the combination of a 4 mm long grating 340 and a lens 336 with 70 mm long focal length would provide a numerical aperture of approximately 0.02 depending on the angle of the grating 340. An optional lenslet array 344 can be used to adjust the numerical aperture of the incident beamlets 341 to match the aperture size and hence the required resolution of the spectrometer 346. In certain embodiments an adjustable polariser 348 can be included to capture a fraction of the power in the combined sample and reference beams according to the expected power levels in each arm, and so interfere the sample and reference light according to their relative phases. Alternatively the polarisation state of the combined beams can be analysed by the polarisation beam splitter (PBS) 350, as is the case with the spectrometer 158 in the apparatus shown in FIG. 1. Inclusion of the polariser 348 allows the polarisations to be analysed substantially independently of the PBS 350.

Figure 5:
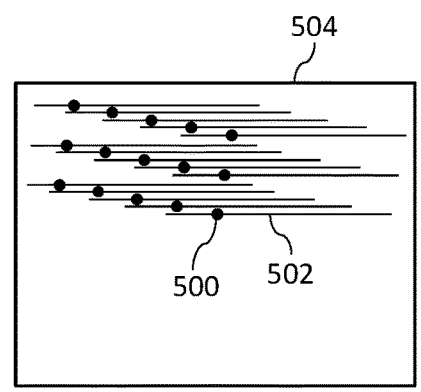
FIG. 5 shows a mapping of a 2-D grid of beamlets dispersed onto a 2-D sensor array.

The dispersion compensated grid of sampling points entering the spectrometer 346 contains sample information derived from reflection or scattering from the illuminated portions of the sample 320, and can be analysed by 2-D spectrometer techniques as described in published US patent application Nos US 2016/0135679 A1 entitled 'Ocular metrology employing spectral wavefront analysis of reflected light' and US 2016/0135680 A1 entitled 'Wavefront analyser', the contents of which are incorporated herein by reference. In the example embodiment depicted in FIG. 3 a compact spectrometer 346 comprises a PBS 350, a flat field relay lens 352 or other focusing element, a wavelength dispersive element in the form of a transmissive grating 356 and a polarisation transformation system 354 comprising a quarter wave plate 358 and a mirror 360. The polarisation transformation system rotates the polarisation state of the dispersed light by 90 degrees to allow redirection at the PBS 350 onto a 2-D sensor array 362 such as a CMOS camera for analysis by a processor 364 equipped with suitable machine-readable program code. The grating 356 is preferably oriented such that the dispersion is at an angle to the sampling grid corresponding to the aperture grid 342, to allow independent interferometry of each resolvable wavelength for each point in the sampling grid. That is, each grid point 500 is dispersed onto a separate set of pixels 502 of a 2-D sensor array 504 as shown in FIG. 5.

Figure 4:
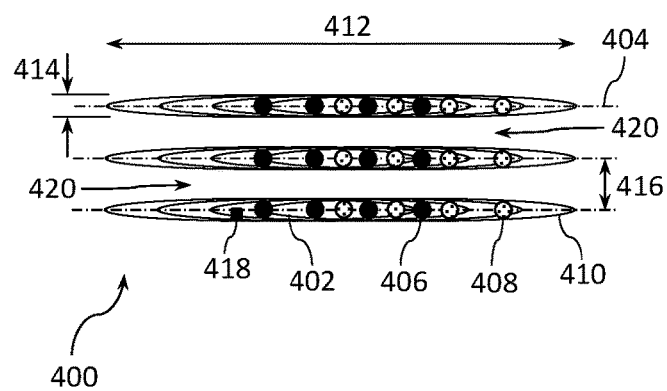
FIG. 4 depicts a spaced-apart set of overlapping wavelength-dispersed lines produced by the FIG. 3 apparatus, for interaction with a sample.

The dimensions of the on-sample dispersed structured illumination field 400 shown in FIG. 4 will depend on the details of the optical components that generate it. In one exemplary embodiment each overlapping sequence of dispersed wavelengths 402 has a length 412 of about 10 mm and a width 414 of about 20 μm, on a centre-to-centre spacing 416 of about 200 μm, with the number of projection lines 404 determined by the number of rows of lenslets in the lenslet array 310. Each point 418 on the sample within one of the overlapping sequences of dispersed wavelengths 402 will be illuminated by multiple wavelengths, which enables interferometric techniques to determine an unambiguous measurement of each axial reflection point over a certain depth using a subsampled spectrum. In embodiments where the grating 306 has optical power, the relative power in the reflection points will be significantly determined by the wavelength dependent focusing. This can provide further information on the reflection points to extend further the range over which an unambiguous determination of depth can be made. Additionally, continuity constraints can often be employed to enhance the relative accuracy of measurements.

We now consider the effect of scanning the dispersed structured illumination field 400 in a controlled fashion relative to the sample 320, e.g. by translating the sample on a stage or by using beam steering optics. After the 2-D sensor array 362 and the processor 364 have acquired and analysed the sample volume corresponding to the spaced apart overlapping sequences of dispersed wavelengths 402 at one set position, the acquisition can be repeated with steps of, say, 10 μm until the spaces 420 between the overlapping sequences are filled, to acquire a complete contiguous volume. A large jump can then be made onto an adjacent sample region and the process repeated. Preferably the steps are made at a small angle to the perpendicular of the projection lines 404 to allow oversampling of each sample point 418 at a different set of wavelengths. It is not essential for the dispersed structured illumination field 400 to have a plurality of overlapping sequences of dispersed wavelengths 402 as shown in FIG. 4, although this would be advantageous for faster measurement of a sample over an extended area. On the other hand the use of a dispersed structured illumination field having only one overlapping sequence of dispersed wavelengths 402, which could for example be produced with a 1-D lenslet array or other 1-D spatial sampling element, may be advantageous for more rapid data readout.

In an alternative embodiment a wavelength-dispersed structured illumination field is generated by interfering an array of wavelength-dispersed beamlets generated for example with a 2-D lenslet array. As described in Besold et al 'Fractional Talbot effect for periodic microlens arrays', Optical Engineering 36(4), 1099-1105 (1997), the coherent superposition of multiple dispersed beamlets forms a grid of high intensity 'rods' which can propagate with coherent superposition over a distance much longer than the corresponding Rayleigh length of an equivalently sized array of individual beamlets.

Although the invention has been described with reference to specific examples, it will be appreciated by those skilled in the art that the invention may be embodied in many other forms.

What is claimed is:

1. A spectrometer for analysing the spectra of a plurality of polarised light beams, said spectrometer comprising:
    a polarisation beam splitter for directing optical power according to polarisation state;
    a wavelength dispersive element for dispersing a plurality of polarised light beams;
    a reflective polarisation state transformer for transforming the polarisation of said plurality of polarised light beams; and
    a two-dimensional sensor array for recording the spectra of said plurality of polarised light beams, wherein said spectrometer is configured such that, in use, said polarisation beam splitter directs incoming polarised light beams to said wavelength dispersive element and said reflective polarisation state transformer and directs the dispersed polarisation transformed light beams to said two-dimensional sensor array.

2. The spectrometer according to 1, wherein said wavelength dispersive element comprises a grating.

3. The spectrometer according to claim 1, wherein said reflective polarisation state transformer comprises a mirror and a quarter wave plate configured such that, in use, said plurality of polarised light beams traverse said quarter wave plate before and after being reflected from said mirror.

4. The spectrometer according to claim 1, wherein said spectrometer comprises a focusing element for imaging the spectral components of said dispersed polarisation transformed light beams onto said two-dimensional sensor array.

5. The spectrometer according to claim 1, wherein said spectrometer comprises a polariser for analysing the polarisation of said plurality of polarised light beams before said polarised light beams traverse said polarisation beam splitter.

6. The spectrometer according to claim 1, wherein said wavelength dispersive element is oriented such that each light beam in said plurality of polarised light beams is dispersed onto a separate set of pixels of said two-dimensional sensor array.

* * * * *